United States Patent [19]
Cheng et al.

[11] Patent Number: 5,981,714
[45] Date of Patent: Nov. 9, 1999

[54] ANTIBODIES SPECIFIC FOR CYSTIC FIBROSIS TRANSMEMBRANE CONDUCTANCE REGULATOR AND USES THEREFOR

[75] Inventors: Seng H. Cheng, Bosaton; John Marshall, Milford; Richard J. Gregory, Ayer; Patrick W. Rafter, Natick, all of Mass.

[73] Assignee: Genzyme Corporation, Cambridge, Mass.

[21] Appl. No.: 08/691,605

[22] Filed: Aug. 15, 1996

Related U.S. Application Data

[63] Continuation of application No. 08/114,950, Aug. 27, 1998, abandoned, which is a continuation-in-part of application No. 08/087,132, Jul. 2, 1993, which is a continuation of application No. 07/613,592, Nov. 15, 1990, abandoned, which is a continuation-in-part of application No. 07/589,295, Sep. 27, 1990, abandoned, which is a continuation-in-part of application No. 07/488,307, Mar. 5, 1990, abandoned.

[51] Int. Cl.$^6$ .............................. C07K 16/28; C12N 5/18
[52] U.S. Cl. ...................... 530/388.2; 435/331; 435/332; 435/7.1; 435/7.21; 530/387.9
[58] Field of Search ............................. 530/388.2, 387.9; 435/331, 332, 7.21, 7.1

[56] References Cited

U.S. PATENT DOCUMENTS 5,240,846   8/1993   Collins et al. .

FOREIGN PATENT DOCUMENTS

| 0 446 017 | 9/1991 | European Pat. Off. . |
|---|---|---|
| WO 91/02796 | 8/1990 | WIPO . |
| WO 91/10734 | 1/1991 | WIPO . |

OTHER PUBLICATIONS

Harlow et al, Antibodies, A Laboratory Manual, Cold Spring Harbor Laboratory, 1988 pp. 60–87, 92–116, 148–150.

Diamond et al, J. Biol. Chem., 266 (33):22761–22769 (1991).

Yorifuji et al., Genomics, 10 : 547–550 (1991).

Tsui, L–C. (1992) "The Spectrum of Cystic Fibrosis Mutations" *Trends in Genetics* 8(11):392–398.

Smith, A.E. (1992) "Emerging Therapies for Cystic Fibrosis" Section V–Topics in Biology in *Ann. Rep. Med. Chem.* 27:235–243.

DiTullio, P. et al (1992) "Production of Cystic Fibrosis Transmembrane Conductance Regulator in the Milk of Transgenic Mice" *Bio/Technology* 10:74–77.

Rosenfeld, M.A. et al. (1992) "In Vivo Transfer of the Human Cystic Fibrosis Transmembrane Conductance Regulator Gene to the Airway Epithelium" *Cell* 68:143–155.

Tilly, B.C. et al. (1992) "Cyclic AMP–Dependent Protein Kinase Activation of Cystic Fibrosis Transmembrane Conductance Regulator Chloride Channels in Planar Lipid Bilayers" *J. Biol. Chem* 267:9470–9473.

Bear, C.E. et al. (1992) "Purification and Functional Reconstitution of the Cystic Fibrosis Transmembrane Conductance Regulator (CFTR)" *Cell* 68:809–818.

Ostedgaard, L.S. and Welsh, M.J. (1992) "Partial Purification of the Cystic Fibrosis Transmembrane Conductance Regulator" *J. Biol. Chem* 267(36):26142–26149.

Denning, G.M. et al. (1992) "Localization of Cystic Fibrosis Transmembrane Conductance Regulator in Chloride Secretory Epithelia" *J. Clin. Invest.* 89:339–349.

Zeitlin, P.L.et al. (1992) "CFTR Protein Expression in Primary and Cultured Epithelia" *Proc. Natl. Acad. Sci. USA* 89:344–347.

Sarkadi, B. et al. (1991) "Biochemical Characterization of the Cystic Fibrosis Transmembrane Conductance Regulator in Normal and Cystic Fibrosis Epithelial Cells" *J. Biol. Chem* 267:2087–2095.

Crawford, I. et al. (1991) "Immunocytochemical Localization of the Cystic Fibrosis Gene Product CFTR" *Proc. Natl. Acad. Sci. USA* 88:9262–9266.

Cheng, S. H. et al. (1991) "Phosphorylation of the R Domain by cAMP–Dependent Protein Kinase Regulates the CFTR Chloride Channel" *Cell* 66:1027–1036.

Gregory, R.J. et al. (1991) "Maturation and Function of Cystic Fibrosis Transmembrane Conductance Regulator Variants Bearing Mutations in Putative Nucleotide–Binding Domains 1 and 2" *Mol. Cell. Biology* 8(11):3886–3893.

Kartner, N. et al. (1991) "Expression of the Cystic Fibrosis Gene in Non–Epithelial Invertebrate Cells Produces a Regulated Anion Conductance" *Cell* 64:681–691.

Dalemans, W. et al. (1991) "Altered Chloride Ion Channel Kinetics Associated with the ΔF508 Cystic Fibrosis Mutation" *Nature* 354:526–528.

Tsui, L–C. et al. (1991) "Biochemical and Molecular Genetics of Cystic Fibrosis" *Advances in Human Genetics* 20:153–266.

Tabcharani, J.A. et al. (1991) "Phosphorylation–Regulated Cl$^-$ Channel in CHO Cells Stably Expressing the Cystic Fibrosis Gene" *Nature* 352:628–631.

(List continued on next page.)

*Primary Examiner*—David L. Fitzgerald
*Attorney, Agent, or Firm*—Baker & Botts, L.L.P.

[57] ABSTRACT

Antibodies for binding epitopes of cystic fibrosis transmembrane conductance regulator (CFTR) and hybridomas which produce such antibodies are described. The antibodies of the present invention can be used in a method for detecting CFTR in a biological sample and/or in a method for purifying CFTR from an impure solution. In addition, the present invention includes a method for detecting CFTR in a biological sample from a nonhuman cystic fibrosis knockout animal wherein the the nonhuman cystic fibrosis knockout animal has been subjected to human CFTR replacement therapy. Another aspect of the present invention is a method for determining the orientation of CFTR in the membrane of a lipid vesicle. Yet another aspect of the invention is a kit for detecting CFTR in a biological sample.

10 Claims, 1 Drawing Sheet

OTHER PUBLICATIONS

Hoogeveen, A.T. et al. (1991) "Immunological Localization of Cystic Fibrosis Candidate Gene Products" *Exp. Cell Res.* 193:435–437.

Marino, C.R. et al. (1991) "Localization of the Cystic Fibrosis Transmembrane Conductance Regulator in Pancreas" *J. Clin. Invest.* 88:712–716.

Rich, D.P. et al. (1990) "Expression of the Cystic Fibrosis Transmembrane Conductance Regulator Corrects Defective Chloride Channel Regulation in Cystic Fibrosis Airway Epithelial Cells" *Nature* 347:358–363.

Cheng, S. H. et al. (1990) "Defective Intracellular Transport and Processing of CFTR is the Molecular Basis of Most Cystic Fibrosis" *Cell* 63:827–834.

Kerem, B.S. et al. (1989) "Identification of the Cystic Fibrosis Gene: Genetic Analysis" *Science* 245:1073–1080.

Li, M. et al. (1988) "Cyclic AMP–dependent Protein Kinase Opens Chloride Channels in Normal but not Cystic Fibrosis Airway Epithelium" *Nature* 331:358–360.

Frizzell, R.A. et al (1986) "Altered Regulation of Airway Epithelial Cell Chloride Channels in Cystic Fibrosis" *Science* 233:558–560.

Gregory, R.J. et al. (1990) "Expression and Characterization of the Cystic Fibrosis Transmembrane Conductance Regulator" *Nature* 347:382–386.

Riordan, J.R. et al. (1989) "Identification of the Cystic Fibrosis Gene: Cloning and Characterization of Complementary DNA" *Science* 245:1066–1073.

Rommens, J.H. et al. (1989) "Characterization of the Cystic Fibrosis Gene: Chromosome Walking and Jumping" *Science* 245: 1059–1065.

Cheng, S.H. et al (1993) "Defective Intracellular Processing of CFTR as the Molecular Basis of Cystic Fibrosis" *Cystic–Fibrosis Current Topics:* vol. 1:175–189.

Teem, J.L. et al. (1993) "Identification of Revertants for the Cystic Fibrosis ΔF508 Mutation Using STE6–CFTR Chimeras in yeast" *Cell* 73:335–346.

Sheppard, D.N. et al. (1993) "Mutations in CFTR Associated with Mild–Disease–Form Cl⁻ Channels With Altered Pore Properties" *Nature* 362:160–164.

Hyde, S.C. et al. (1993) "Correction of the Ion Transport Defect in Cystic Fibrosis Transgenic Mice by Gene Therapy" *Nature* 362:250–255.

Denning, G.M. et al. (1992) "Abnormal Localization of Cystic Fibrosis Transmembrane Conductance Regulator in Primary Cultures of Cystic Fibrosis Airway Epithelia" *J. Cell Biol.* 118(3):551–559.

Thomas, P.J. et al. (1992) "The Cystic Fibrosis Transmembrane Conductance" *J. Biol. Chem* 267(9):5727–5730.

Welsh, M.J. (1992) "Cystic Fibrosis Transmembrane Conductance Regulator: A Chloride Channel with Novel Regulation" *Neuron* 8:821–829.

Denning, G.M. et al (1992) "Processing of Mutant Cystic Fibrosis Transmembrane Conductance Regulator is Temperature–Sensitive" *Nature* 358:761–764.

Kartner, N. et al. (1992) "Mislocalization of ΔF508 CFTR in Cystic Fibrosis Sweat Gland" *Nature Genetics* 1:321–327.

J. Jacquot et al., "Localization of the Cystic Fibrosis Transmembrane Conductance Regulator in Airway Secretory Glands", *European Respiratory Journal,* 6, 1993, pp. 169–176.

M. Malcolm et al., "Characterization of Anti–peptide CFTR Antibodies", *Biochemical Society Transactions,* 19, 1991, p. 247S.

S. McGrath, et al., "Cystic Fibrosis Gene and Protein Expression During Fetal Lung Development", *American Journal of Respiratory Cellular and Molecular Biology,* 8, 1993, pp. 201–208.

Fuller, C.M. et al. (1992) "Antibodies Against the Cytsic Fibrosis Transmembrane Regulator" *Am. J. Physiol.* 262:396–404.

Cohn, J.A. et al. (1991) "CFTR: Development of High Affinity Antibodies and Localization in Sweat Gland" *Biochem. Biophys. Res. Comm.* 181(1):36–43.

Pereira, M.M.C. et al. (1991) "Characterization of Anti–Peptide CFTR Antibodies" *Biochem. Soc. Trans.* 19:2475.

```
                           SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
         (A) LENGTH: 6129 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 133..4572

(xi) SEQUENCE DESCRIPTION: SEQ ID NO:1:

AATTGGAAGC AAATGACATC ACAGCAGGTC AGAGAAAAAG GGTTGAGCGG CAGGCACCCA       60

GAGTAGTAGG TCTTTGGCAT TAGGAGCTTG AGCCCAGACG GCCCTAGCAG GGACCCCAGC      120

GCCCGAGAGA CC ATG CAG AGG TCG CCT CTG GAA AAG GCC AGC GTT GTC         168
              Met Gln Arg Ser Pro Leu Glu Lys Ala Ser Val Val
                1               5                  10
```

| | | |
|---|---|---|
| TCC AAA CTT TTT TTC AGC TGG ACC AGA CCA ATT TTG AGG AAA GGA TAC<br>Ser Lys Leu Phe Phe Ser Trp Thr Arg Pro Ile Leu Arg Lys Gly Tyr<br>        15                  20                    25 | 216 |
| AGA CAG CGC CTG GAA TTG TCA GAC ATA TAC CAA ATC CCT TCT GTT GAT<br>Arg Gln Arg Leu Glu Leu Ser Asp Ile Tyr Gln Ile Pro Ser Val Asp<br>       30                  35                    40 | 264 |
| TCT GCT GAC AAT CTA TCT GAA AAA TTG GAA AGA GAA TGG GAT AGA GAG<br>Ser Ala Asp Asn Leu Ser Glu Lys Leu Glu Arg Glu Trp Asp Arg Glu<br>45                  50                  55                    60 | 312 |
| CTG GCT TCA AAG AAA AAT CCT AAA CTC ATT AAT GCC CTT CGG CGA TGT<br>Leu Ala Ser Lys Lys Asn Pro Lys Leu Ile Asn Ala Leu Arg Arg Cys<br>                  65                  70                  75 | 360 |
| TTT TTC TGG AGA TTT ATG TTC TAT GGA ATC TTT TTA TAT TTA GGG GAA<br>Phe Phe Trp Arg Phe Met Phe Tyr Gly Ile Phe Leu Tyr Leu Gly Glu<br>                  80                  85                  90 | 408 |
| GTC ACC AAA GCA GTA CAG CCT CTC TTA CTG GGA AGA ATC ATA GCT TCC<br>Val Thr Lys Ala Val Gln Pro Leu Leu Leu Gly Arg Ile Ile Ala Ser<br>       95                     100                 105 | 456 |
| TAT GAC CCG GAT AAC AAG GAG GAA CGC TCT ATC GCG ATT TAT CTA GGC<br>Tyr Asp Pro Asp Asn Lys Glu Glu Arg Ser Ile Ala Ile Tyr Leu Gly<br>       110                 115                120 | 504 |
| ATA GGC TTA TGC CTT CTC TTT ATT GTG AGG ACA CTG CTC CTA CAC CCA<br>Ile Gly Leu Cys Leu Leu Phe Ile Val Arg Thr Leu Leu Leu His Pro<br>125                 130                135                140 | 552 |
| GCC ATT TTT GGC CTT CAT CAC ATT GGA ATG CAG ATG AGA ATA GCT ATG<br>Ala Ile Phe Gly Leu His His Ile Gly Met Gln Met Arg Ile Ala Met<br>                 145                150                155 | 600 |
| TTT AGT TTG ATT TAT AAG AAG ACT TTA AAG CTG TCA AGC CGT GTT CTA<br>Phe Ser Leu Ile Tyr Lys Lys Thr Leu Lys Leu Ser Ser Arg Val Leu<br>                 160                165                170 | 648 |
| GAT AAA ATA AGT ATT GGA CAA CTT GTT AGT CTC CTT TCC AAC AAC CTG<br>Asp Lys Ile Ser Ile Gly Gln Leu Val Ser Leu Leu Ser Asn Asn Leu<br>       175                 180                185 | 696 |
| AAC AAA TTT GAT GAA GGA CTT GCA TTG GCA CAT TTC GTG TGG ATC GCT<br>Asn Lys Phe Asp Glu Gly Leu Ala Leu Ala His Phe Val Trp Ile Ala<br>       190                 195                200 | 744 |
| CCT TTG CAA GTG GCA CTC CTC ATG GGG CTA ATC TGG GAG TTG TTA CAG<br>Pro Leu Gln Val Ala Leu Leu Met Gly Leu Ile Trp Glu Leu Leu Gln<br>205                 210                215                220 | 792 |
| GCG TCT GCC TTC TGT GGA CTT GGT TTC CTG ATA GTC CTT GCC CTT TTT<br>Ala Ser Ala Phe Cys Gly Leu Gly Phe Leu Ile Val Leu Ala Leu Phe<br>                 225                230                235 | 840 |
| CAG GCT GGG CTA GGG AGA ATG ATG ATG AAG TAC AGA GAT CAG AGA GCT<br>Gln Ala Gly Leu Gly Arg Met Met Met Lys Tyr Arg Asp Gln Arg Ala<br>                 240                245                250 | 888 |
| GGG AAG ATC AGT GAA AGA CTT GTG ATT ACC TCA GAA ATG ATT GAA AAT<br>Gly Lys Ile Ser Glu Arg Leu Val Ile Thr Ser Glu Met Ile Glu Asn<br>       255                 260                265 | 936 |
| ATC CAA TCT GTT AAG GCA TAC TGC TGG GAA GAA GCA ATG GAA AAA ATG<br>Ile Gln Ser Val Lys Ala Tyr Cys Trp Glu Glu Ala Met Glu Lys Met<br>270                 275                280 | 984 |
| ATT GAA AAC TTA AGA CAA ACA GAA CTG AAA CTG ACT CGG AAG GCA GCC<br>Ile Glu Asn Leu Arg Gln Thr Glu Leu Lys Leu Thr Arg Lys Ala Ala<br>285                 290                295                300 | 1032 |
| TAT GTG AGA TAC TTC AAT AGC TCA GCC TTC TTC TTC TCA GGG TTC TTT<br>Tyr Val Arg Tyr Phe Asn Ser Ser Ala Phe Phe Phe Ser Gly Phe Phe<br>                 305                310                315 | 1080 |
| GTG GTG TTT TTA TCT GTG CTT CCC TAT GCA CTA ATC AAA GGA ATC ATC<br>Val Val Phe Leu Ser Val Leu Pro Tyr Ala Leu Ile Lys Gly Ile Ile<br>                 320                325                330 | 1128 |

| | |
|---|---|
| CTC CGG AAA ATA TTC ACC ACC ATC TCA TTC TGC ATT GTT CTG CGC ATG<br>Leu Arg Lys Ile Phe Thr Thr Ile Ser Phe Cys Ile Val Leu Arg Met<br>335 340 345 | 1176 |
| GCG GTC ACT CGG CAA TTT CCC TGG GCT GTA CAA ACA TGG TAT GAC TCT<br>Ala Val Thr Arg Gln Phe Pro Trp Ala Val Gln Thr Trp Tyr Asp Ser<br>350 355 360 | 1224 |
| CTT GGA GCA ATA AAC AAA ATA CAG GAT TTC TTA CAA AAG CAA GAA TAT<br>Leu Gly Ala Ile Asn Lys Ile Gln Asp Phe Leu Gln Lys Gln Glu Tyr<br>365 370 375 380 | 1272 |
| AAG ACA TTG GAA TAT AAC TTA ACG ACT ACA GAA GTA GTG ATG GAG AAT<br>Lys Thr Leu Glu Tyr Asn Leu Thr Thr Thr Glu Val Val Met Glu Asn<br>385 390 395 | 1320 |
| GTA ACA GCC TTC TGG GAG GAG GGA TTT GGG GAA TTA TTT GAG AAA GCA<br>Val Thr Ala Phe Trp Glu Glu Gly Phe Gly Glu Leu Phe Glu Lys Ala<br>400 405 410 | 1368 |
| AAA CAA AAC AAT AAC AAT AGA AAA ACT TCT AAT GGT GAT GAC AGC CTC<br>Lys Gln Asn Asn Asn Asn Arg Lys Thr Ser Asn Gly Asp Asp Ser Leu<br>415 420 425 | 1416 |
| TTC TTC AGT AAT TTC TCA CTT CTT GGT ACT CCT GTC CTG AAA GAT ATT<br>Phe Phe Ser Asn Phe Ser Leu Leu Gly Thr Pro Val Leu Lys Asp Ile<br>430 435 440 | 1464 |
| AAT TTC AAG ATA GAA AGA GGA CAG TTG TTG GCG GTT GCT GGA TCC ACT<br>Asn Phe Lys Ile Glu Arg Gly Gln Leu Leu Ala Val Ala Gly Ser Thr<br>445 450 455 460 | 1512 |
| GGA GCA GGC AAG ACT TCA CTT CTA ATG ATG ATT ATG GGA GAA CTG GAG<br>Gly Ala Gly Lys Thr Ser Leu Leu Met Met Ile Met Gly Glu Leu Glu<br>465 470 475 | 1560 |
| CCT TCA GAG GGT AAA ATT AAG CAC AGT GGA AGA ATT TCA TTC TGT TCT<br>Pro Ser Glu Gly Lys Ile Lys His Ser Gly Arg Ile Ser Phe Cys Ser<br>480 485 490 | 1608 |
| CAG TTT TCC TGG ATT ATG CCT GGC ACC ATT AAA GAA AAT ATC ATC TTT<br>Gln Phe Ser Trp Ile Met Pro Gly Thr Ile Lys Glu Asn Ile Ile Phe<br>495 500 505 | 1656 |
| GGT GTT TCC TAT GAT GAA TAT AGA TAC AGA AGC GTC ATC AAA GCA TGC<br>Gly Val Ser Tyr Asp Glu Tyr Arg Tyr Arg Ser Val Ile Lys Ala Cys<br>510 515 520 | 1704 |
| CAA CTA GAA GAG GAC ATC TCC AAG TTT GCA GAG AAA GAC AAT ATA GTT<br>Gln Leu Glu Glu Asp Ile Ser Lys Phe Ala Glu Lys Asp Asn Ile Val<br>525 530 535 540 | 1752 |
| CTT GGA GAA GGT GGA ATC ACA CTG AGT GGA GGT CAA CGA GCA AGA ATT<br>Leu Gly Glu Gly Gly Ile Thr Leu Ser Gly Gly Gln Arg Ala Arg Ile<br>545 550 555 | 1800 |
| TCT TTA GCA AGA GCA GTA TAC AAA GAT GCT GAT TTG TAT TTA TTA GAC<br>Ser Leu Ala Arg Ala Val Tyr Lys Asp Ala Asp Leu Tyr Leu Leu Asp<br>560 565 570 | 1848 |
| TCT CCT TTT GGA TAC CTA GAT GTT TTA ACA GAA AAA GAA ATA TTT GAA<br>Ser Pro Phe Gly Tyr Leu Asp Val Leu Thr Glu Lys Glu Ile Phe Glu<br>575 580 585 | 1896 |
| AGC TGT GTC TGT AAA CTG ATG GCT AAC AAA ACT AGG ATT TTG GTC ACT<br>Ser Cys Val Cys Lys Leu Met Ala Asn Lys Thr Arg Ile Leu Val Thr<br>590 595 600 | 1944 |
| TCT AAA ATG GAA CAT TTA AAG AAA GCT GAC AAA ATA TTA ATT TTG CAT<br>Ser Lys Met Glu His Leu Lys Lys Ala Asp Lys Ile Leu Ile Leu His<br>605 610 615 620 | 1992 |
| GAA GGT AGC AGC TAT TTT TAT GGG ACA TTT TCA GAA CTC CAA AAT CTA<br>Glu Gly Ser Ser Tyr Phe Tyr Gly Thr Phe Ser Glu Leu Gln Asn Leu<br>625 630 635 | 2040 |
| CAG CCA GAC TTT AGC TCA AAA CTC ATG GGA TGT GAT TCT TTC GAC CAA<br>Gln Pro Asp Phe Ser Ser Lys Leu Met Gly Cys Asp Ser Phe Asp Gln<br>640 645 650 | 2088 |

-continued

| | | | | | | | | | | | | | | | | |
|---|---|---|---|---|---|---|---|---|---|---|---|---|---|---|---|---|
| TTT | AGT | GCA | GAA | AGA | AGA | AAT | TCA | ATC | CTA | ACT | GAG | ACC | TTA | CAC | CGT | 2136 |
| Phe | Ser | Ala | Glu | Arg | Arg | Asn | Ser | Ile | Leu | Thr | Glu | Thr | Leu | His | Arg | |
| | | 655 | | | | 660 | | | | 665 | | | | | | |
| TTC | TCA | TTA | GAA | GGA | GAT | GCT | CCT | GTC | TCC | TGG | ACA | GAA | ACA | AAA | AAA | 2184 |
| Phe | Ser | Leu | Glu | Gly | Asp | Ala | Pro | Val | Ser | Trp | Thr | Glu | Thr | Lys | Lys | |
| 670 | | | | 675 | | | | 680 | | | | | | | | |
| CAA | TCT | TTT | AAA | CAG | ACT | GGA | GAG | TTT | GGG | GAA | AAA | AGG | AAG | AAT | TCT | 2232 |
| Gln | Ser | Phe | Lys | Gln | Thr | Gly | Glu | Phe | Gly | Glu | Lys | Arg | Lys | Asn | Ser | |
| 685 | | | | 690 | | | | 695 | | | | | | | 700 | |
| ATT | CTC | AAT | CCA | ATC | AAC | TCT | ATA | CGA | AAA | TTT | TCC | ATT | GTG | CAA | AAG | 2280 |
| Ile | Leu | Asn | Pro | Ile | Asn | Ser | Ile | Arg | Lys | Phe | Ser | Ile | Val | Gln | Lys | |
| | | | | 705 | | | | 710 | | | | 715 | | | | |
| ACT | CCC | TTA | CAA | ATG | AAT | GGC | ATC | GAA | GAG | GAT | TCT | GAT | GAG | CCT | TTA | 2328 |
| Thr | Pro | Leu | Gln | Met | Asn | Gly | Ile | Glu | Glu | Asp | Ser | Asp | Glu | Pro | Leu | |
| | | 720 | | | | 725 | | | | 730 | | | | | | |
| GAG | AGA | AGG | CTG | TCC | TTA | GTA | CCA | GAT | TCT | GAG | CAG | GGA | GAG | GCG | ATA | 2376 |
| Glu | Arg | Arg | Leu | Ser | Leu | Val | Pro | Asp | Ser | Glu | Gln | Gly | Glu | Ala | Ile | |
| | | 735 | | | | 740 | | | | 745 | | | | | | |
| CTG | CCT | CGC | ATC | AGC | GTG | ATC | AGC | ACT | GGC | CCC | ACG | CTT | CAG | GCA | CGA | 2424 |
| Leu | Pro | Arg | Ile | Ser | Val | Ile | Ser | Thr | Gly | Pro | Thr | Leu | Gln | Ala | Arg | |
| | | 750 | | | | 755 | | | | 760 | | | | | | |
| AGG | AGG | CAG | TCT | GTC | CTG | AAC | CTG | ATG | ACA | CAC | TCA | GTT | AAC | CAA | GGT | 2472 |
| Arg | Arg | Gln | Ser | Val | Leu | Asn | Leu | Met | Thr | His | Ser | Val | Asn | Gln | Gly | |
| 765 | | | | 770 | | | | 775 | | | | | | | 780 | |
| CAG | AAC | ATT | CAC | CGA | AAG | ACA | ACA | GCA | TCC | ACA | CGA | AAA | GTG | TCA | CTG | 2520 |
| Gln | Asn | Ile | His | Arg | Lys | Thr | Thr | Ala | Ser | Thr | Arg | Lys | Val | Ser | Leu | |
| | | | | 785 | | | | 790 | | | | 795 | | | | |
| GCC | CCT | CAG | GCA | AAC | TTG | ACT | GAA | CTG | GAT | ATA | TAT | TCA | AGA | AGG | TTA | 2568 |
| Ala | Pro | Gln | Ala | Asn | Leu | Thr | Glu | Leu | Asp | Ile | Tyr | Ser | Arg | Arg | Leu | |
| | | 800 | | | | 805 | | | | 810 | | | | | | |
| TCT | CAA | GAA | ACT | GGC | TTG | GAA | ATA | AGT | GAA | GAA | ATT | AAC | GAA | GAA | GAC | 2616 |
| Ser | Gln | Glu | Thr | Gly | Leu | Glu | Ile | Ser | Glu | Glu | Ile | Asn | Glu | Glu | Asp | |
| | | 815 | | | | 820 | | | | 825 | | | | | | |
| TTA | AAG | GAG | TGC | CTT | TTT | GAT | GAT | ATG | GAG | AGC | ATA | CCA | GCA | GTG | ACT | 2664 |
| Leu | Lys | Glu | Cys | Leu | Phe | Asp | Asp | Met | Glu | Ser | Ile | Pro | Ala | Val | Thr | |
| 830 | | | | 835 | | | | 840 | | | | | | | | |
| ACA | TGG | AAC | ACA | TAC | CTT | CGA | TAT | ATT | ACT | GTC | CAC | AAG | AGC | TTA | ATT | 2712 |
| Thr | Trp | Asn | Thr | Tyr | Leu | Arg | Tyr | Ile | Thr | Val | His | Lys | Ser | Leu | Ile | |
| 845 | | | | 850 | | | | 855 | | | | | | | 860 | |
| TTT | GTG | CTA | ATT | TGG | TGC | TTA | GTA | ATT | TTT | CTG | GCA | GAG | GTG | GCT | GCT | 2760 |
| Phe | Val | Leu | Ile | Trp | Cys | Leu | Val | Ile | Phe | Leu | Ala | Glu | Val | Ala | Ala | |
| | | | | 865 | | | | 870 | | | | 875 | | | | |
| TCT | TTG | GTT | GTG | CTG | TGG | CTC | CTT | GGA | AAC | ACT | CCT | CTT | CAA | GAC | AAA | 2808 |
| Ser | Leu | Val | Val | Leu | Trp | Leu | Leu | Gly | Asn | Thr | Pro | Leu | Gln | Asp | Lys | |
| | | | | 880 | | | | 885 | | | | 890 | | | | |
| GGG | AAT | AGT | ACT | CAT | AGT | AGA | AAT | AAC | AGC | TAT | GCA | GTG | ATT | ATC | ACC | 2856 |
| Gly | Asn | Ser | Thr | His | Ser | Arg | Asn | Asn | Ser | Tyr | Ala | Val | Ile | Ile | Thr | |
| | | 895 | | | | 900 | | | | 905 | | | | | | |
| AGC | ACC | AGT | TCG | TAT | TAT | GTG | TTT | TAC | ATT | TAC | GTG | GGA | GTA | GCC | GAC | 2904 |
| Ser | Thr | Ser | Ser | Tyr | Tyr | Val | Phe | Tyr | Ile | Tyr | Val | Gly | Val | Ala | Asp | |
| | | 910 | | | | 915 | | | | 920 | | | | | | |
| ACT | TTG | CTT | GCT | ATG | GGA | TTC | TTC | AGA | GGT | CTA | CCA | CTG | GTG | CAT | ACT | 2952 |
| Thr | Leu | Leu | Ala | Met | Gly | Phe | Phe | Arg | Gly | Leu | Pro | Leu | Val | His | Thr | |
| 925 | | | | 930 | | | | 935 | | | | | | | 940 | |
| CTA | ATC | ACA | GTG | TCG | AAA | ATT | TTA | CAC | CAC | AAA | ATG | TTA | CAT | TCT | GTT | 3000 |
| Leu | Ile | Thr | Val | Ser | Lys | Ile | Leu | His | His | Lys | Met | Leu | His | Ser | Val | |
| | | | | 945 | | | | 950 | | | | 955 | | | | |
| CTT | CAA | GCA | CCT | ATG | TCA | ACC | CTC | AAC | ACG | TTG | AAA | GCA | GGT | GGG | ATT | 3048 |
| Leu | Gln | Ala | Pro | Met | Ser | Thr | Leu | Asn | Thr | Leu | Lys | Ala | Gly | Gly | Ile | |
| | | 960 | | | | 965 | | | | 970 | | | | | | |

-continued

| | | |
|---|---|---|
| CTT AAT AGA TTC TCC AAA GAT ATA GCA ATT TTG GAT GAC CTT CTG CCT<br>Leu Asn Arg Phe Ser Lys Asp Ile Ala Ile Leu Asp Asp Leu Leu Pro<br>        975                    980                   985 | 3096 |
| CTT ACC ATA TTT GAC TTC ATC CAG TTG TTA TTA ATT GTG ATT GGA GCT<br>Leu Thr Ile Phe Asp Phe Ile Gln Leu Leu Leu Ile Val Ile Gly Ala<br>990                    995                    1000 | 3144 |
| ATA GCA GTT GTC GCA GTT TTA CAA CCC TAC ATC TTT GTT GCA ACA GTG<br>Ile Ala Val Val Ala Val Leu Gln Pro Tyr Ile Phe Val Ala Thr Val<br>1005                  1010                 1015                 1020 | 3192 |
| CCA GTG ATA GTG GCT TTT ATT ATG TTG AGA GCA TAT TTC CTC CAA ACC<br>Pro Val Ile Val Ala Phe Ile Met Leu Arg Ala Tyr Phe Leu Gln Thr<br>                   1025                 1030                 1035 | 3240 |
| TCA CAG CAA CTC AAA CAA CTG GAA TCT GAA GGC AGG AGT CCA ATT TTC<br>Ser Gln Gln Leu Lys Gln Leu Glu Ser Glu Gly Arg Ser Pro Ile Phe<br>                  1040                1045                1050 | 3288 |
| ACT CAT CTT GTT ACA AGC TTA AAA GGA CTA TGG ACA CTT CGT GCC TTC<br>Thr His Leu Val Thr Ser Leu Lys Gly Leu Trp Thr Leu Arg Ala Phe<br>                 1055                 1060                 1065 | 3336 |
| GGA CGG CAG CCT TAC TTT GAA ACT CTG TTC CAC AAA GCT CTG AAT TTA<br>Gly Arg Gln Pro Tyr Phe Glu Thr Leu Phe His Lys Ala Leu Asn Leu<br>                  1070                1075                1080 | 3384 |
| CAT ACT GCC AAC TGG TTC TTG TAC CTG TCA ACA CTG CGC TGG TTC CAA<br>His Thr Ala Asn Trp Phe Leu Tyr Leu Ser Thr Leu Arg Trp Phe Gln<br>1085                  1090                 1095                 1100 | 3432 |
| ATG AGA ATA GAA ATG ATT TTT GTC ATC TTC TTC ATT GCT GTT ACC TTC<br>Met Arg Ile Glu Met Ile Phe Val Ile Phe Phe Ile Ala Val Thr Phe<br>                   1105                 1110                 1115 | 3480 |
| ATT TCC ATT TTA ACA ACA GGA GAA GGA GAA GGA AGA GTT GGT ATT ATC<br>Ile Ser Ile Leu Thr Thr Gly Glu Gly Glu Gly Arg Val Gly Ile Ile<br>                  1120                1125                1130 | 3528 |
| CTG ACT TTA GCC ATG AAT ATC ATG AGT ACA TTG CAG TGG GCT GTA AAC<br>Leu Thr Leu Ala Met Asn Ile Met Ser Thr Leu Gln Trp Ala Val Asn<br>                 1135                 1140                 1145 | 3576 |
| TCC AGC ATA GAT GTG GAT AGC TTG ATG CGA TCT GTG AGC CGA GTC TTT<br>Ser Ser Ile Asp Val Asp Ser Leu Met Arg Ser Val Ser Arg Val Phe<br>                  1150                1155                1160 | 3624 |
| AAG TTC ATT GAC ATG CCA ACA GAA GGT AAA CCT ACC AAG TCA ACC AAA<br>Lys Phe Ile Asp Met Pro Thr Glu Gly Lys Pro Thr Lys Ser Thr Lys<br>1165                  1170                 1175                 1180 | 3672 |
| CCA TAC AAG AAT GGC CAA CTC TCG AAA GTT ATG ATT ATT GAG AAT TCA<br>Pro Tyr Lys Asn Gly Gln Leu Ser Lys Val Met Ile Ile Glu Asn Ser<br>                  1185                1190                1195 | 3720 |
| CAC GTG AAG AAA GAT GAC ATC TGG CCC TCA GGG GGC CAA ATG ACT GTC<br>His Val Lys Lys Asp Asp Ile Trp Pro Ser Gly Gly Gln Met Thr Val<br>                 1200                 1205                 1210 | 3768 |
| AAA GAT CTC ACA GCA AAA TAC ACA GAA GGT GGA AAT GCC ATA TTA GAG<br>Lys Asp Leu Thr Ala Lys Tyr Thr Glu Gly Gly Asn Ala Ile Leu Glu<br>                 1215                 1220                 1225 | 3816 |
| AAC ATT TCC TTC TCA ATA AGT CCT GGC CAG AGG GTG GGC CTC TTG GGA<br>Asn Ile Ser Phe Ser Ile Ser Pro Gly Gln Arg Val Gly Leu Leu Gly<br>1230                  1235                 1240 | 3864 |
| AGA ACT GGA TCA GGG AAG AGT ACT TTG TTA TCA GCT TTT TTG AGA CTA<br>Arg Thr Gly Ser Gly Lys Ser Thr Leu Leu Ser Ala Phe Leu Arg Leu<br>1245                  1250                 1255                 1260 | 3912 |
| CTG AAC ACT GAA GGA GAA ATC CAG ATC GAT GGT GTG TCT TGG GAT TCA<br>Leu Asn Thr Glu Gly Glu Ile Gln Ile Asp Gly Val Ser Trp Asp Ser<br>                  1265                 1270                 1275 | 3960 |
| ATA ACT TTG CAA CAG TGG AGG AAA GCC TTT GGA GTG ATA CCA CAG AAA<br>Ile Thr Leu Gln Gln Trp Arg Lys Ala Phe Gly Val Ile Pro Gln Lys<br>                  1280                1285                1290 | 4008 |

| | |
|---|---|
| GTA TTT ATT TTT TCT GGA ACA TTT AGA AAA AAC TTG GAT CCC TAT GAA<br>Val Phe Ile Phe Ser Gly Thr Phe Arg Lys Asn Leu Asp Pro Tyr Glu<br>           1295                     1300                  1305 | 4056 |
| CAG TGG AGT GAT CAA GAA ATA TGG AAA GTT GCA GAT GAG GTT GGG CTC<br>Gln Trp Ser Asp Gln Glu Ile Trp Lys Val Ala Asp Glu Val Gly Leu<br>1310                  1315                  1320 | 4104 |
| AGA TCT GTG ATA GAA CAG TTT CCT GGG AAG CTT GAC TTT GTC CTT GTG<br>Arg Ser Val Ile Glu Gln Phe Pro Gly Lys Leu Asp Phe Val Leu Val<br>1325                  1330                  1335                  1340 | 4152 |
| GAT GGG GGC TGT GTC CTA AGC CAT GGC CAC AAG CAG TTG ATG TGC TTG<br>Asp Gly Gly Cys Val Leu Ser His Gly His Lys Gln Leu Met Cys Leu<br>           1345                     1350                  1355 | 4200 |
| GCT AGA TCT GTT CTC AGT AAG GCG AAG ATC TTG CTG CTT GAT GAA CCC<br>Ala Arg Ser Val Leu Ser Lys Ala Lys Ile Leu Leu Leu Asp Glu Pro<br>                 1360                  1365                  1370 | 4248 |
| AGT GCT CAT TTG GAT CCA GTA ACA TAC CAA ATA ATT AGA AGA ACT CTA<br>Ser Ala His Leu Asp Pro Val Thr Tyr Gln Ile Ile Arg Arg Thr Leu<br>           1375                     1380                  1385 | 4296 |
| AAA CAA GCA TTT GCT GAT TGC ACA GTA ATT CTC TGT GAA CAC AGG ATA<br>Lys Gln Ala Phe Ala Asp Cys Thr Val Ile Leu Cys Glu His Arg Ile<br>           1390                     1395                  1400 | 4344 |
| GAA GCA ATG CTG GAA TGC CAA CAA TTT TTG GTC ATA GAA GAG AAC AAA<br>Glu Ala Met Leu Glu Cys Gln Gln Phe Leu Val Ile Glu Glu Asn Lys<br>1405                  1410                  1415                  1420 | 4392 |
| GTG CGG CAG TAC GAT TCC ATC CAG AAA CTG CTG AAC GAG AGG AGC CTC<br>Val Arg Gln Tyr Asp Ser Ile Gln Lys Leu Leu Asn Glu Arg Ser Leu<br>                 1425                  1430                  1435 | 4440 |
| TTC CGG CAA GCC ATC AGC CCC TCC GAC AGG GTG AAG CTC TTT CCC CAC<br>Phe Arg Gln Ala Ile Ser Pro Ser Asp Arg Val Lys Leu Phe Pro His<br>           1440                     1445                  1450 | 4488 |
| CGG AAC TCA AGC AAG TGC AAG TCT AAG CCC CAG ATT GCT GCT CTG AAA<br>Arg Asn Ser Ser Lys Cys Lys Ser Lys Pro Gln Ile Ala Ala Leu Lys<br>           1455                     1460                  1465 | 4536 |
| GAG GAG ACA GAA GAA GAG GTG CAA GAT ACA AGG CTT TAGAGAGCAG<br>Glu Glu Thr Glu Glu Glu Val Gln Asp Thr Arg Leu<br>1470                  1475                  1480 | 4582 |
| CATAAATGTT GACATGGGAC ATTTGCTCAT GGAATTGGAG CTCGTGGGAC AGTCACCTCA | 4642 |
| TGGAATTGGA GCTCGTGGAA CAGTTACCTC TGCCTCAGAA AACAAGGATG AATTAAGTTT | 4702 |
| TTTTTTAAAA AAGAAACATT TGGTAAGGGG AATTGAGGAC ACTGATATGG GTCTTGATAA | 4762 |
| ATGGCTTCCT GGCAATAGTC AAATTGTGTG AAAGGTACTT CAAATCCTTG AAGATTTACC | 4822 |
| ACTTGTGTTT TGCAAGCCAG ATTTTCCTGA AAACCCTTGC CATGTGCTAG TAATTGGAAA | 4882 |
| GGCAGCTCTA AATGTCAATC AGCCTAGTTG ATCAGCTTAT TGTCTAGTGA AACTCGTTAA | 4942 |
| TTTGTAGTGT TGGAGAAGAA CTGAAATCAT ACTTCTTAGG GTTATGATTA AGTAATGATA | 5002 |
| ACTGGAAACT TCAGCGGTTT ATATAAGCTT GTATTCCTTT TTCTCTCCTC TCCCCATGAT | 5062 |
| GTTTAGAAAC ACAACTATAT TGTTTGCTAA GCATTCCAAC TATCTCATTT CCAAGCAAGT | 5122 |
| ATTAGAATAC CACAGGAACC ACAAGACTGC ACATCAAAAT ATGCCCCATT CAACATCTAG | 5182 |
| TGAGCAGTCA GGAAAGAGAA CTTCCAGATC CTGGAAATCA GGGTTAGTAT TGTCCAGGTC | 5242 |
| TACCAAAAAT CTCAATATTT CAGATAATCA CAATACATCC CTTACCTGGG AAAGGGCTGT | 5302 |
| TATAATCTTT CACAGGGGAC AGGATGGTTC CCTTGATGAA GAAGTTGATA TGCCTTTTCC | 5362 |
| CAACTCCAGA AAGTGACAAG CTCACAGACC TTTGAACTAG AGTTTAGCTG GAAAAGTATG | 5422 |
| TTAGTGCAAA TTGTCACAGG ACAGCCCTTC TTTCCACAGA AGCTCCAGGT AGAGGGTGTG | 5482 |
| TAAGTAGATA GGCCATGGGC ACTGTGGGTA GACACACATG AAGTCCAAGC ATTTAGATGT | 5542 |

-continued

```
ATAGGTTGAT GGTGGTATGT TTTCAGGCTA GATGTATGTA CTTCATGCTG TCTACACTAA    5602

GAGAGAATGA GAGACACACT GAAGAAGCAC CAATCATGAA TTAGTTTTAT ATGCTTCTGT    5662

TTTATAATTT TGTGAAGCAA AATTTTTTCT CTAGGAAATA TTTATTTTAA TAATGTTTCA    5722

AACATATATT ACAATGCTGT ATTTTAAAAG AATGATTATG AATTACATTT GTATAAAATA    5782

ATTTTTATAT TTGAAATATT GACTTTTTAT GGCACTAGTA TTTTTATGAA ATATTATGTT    5842

AAAACTGGGA CAGGGGAGAA CCTAGGGTGA TATTAACCAG GGGCCATGAA TCACCTTTTG    5902

GTCTGGAGGG AAGCCTTGGG GCTGATCGAG TTGTTGCCCA CAGCTGTATG ATTCCCAGCC    5962

AGACACAGCC TCTTAGATGC AGTTCTGAAG AAGATGGTAC CACCAGTCTG ACTGTTTCCA    6022

TCAAGGGTAC ACTGCCTTCT CAACTCCAAA CTGACTCTTA AGAAGACTGC ATTATATTTA    6082

TTACTGTAAG AAAATATCAC TTGTCAATAA AATCCATACA TTTGTGT                 6129
```

(2) INFORMATION FOR SEQ ID NO:2:

(i) SEQUENCE CHARACTERISTICS:
        (A) LENGTH: 1480 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255
```

```
Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
            290                 295                 300

Phe Asn Ser Ser Ala Phe Phe Phe Ser Gly Phe Phe Val Val Phe Leu
305                     310                 315                 320

Ser Val Leu Pro Tyr Ala Leu Ile Lys Gly Ile Ile Leu Arg Lys Ile
                    325                 330                 335

Phe Thr Thr Ile Ser Phe Cys Ile Val Leu Arg Met Ala Val Thr Arg
                    340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
            370                 375                 380

Tyr Asn Leu Thr Thr Thr Glu Val Val Met Glu Asn Val Thr Ala Phe
385                     390                 395                 400

Trp Glu Glu Gly Phe Gly Glu Leu Phe Glu Lys Ala Lys Gln Asn Asn
                    405                 410                 415

Asn Asn Arg Lys Thr Ser Asn Gly Asp Asp Ser Leu Phe Phe Ser Asn
                    420                 425                 430

Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
            450                 455                 460

Thr Ser Leu Leu Met Met Ile Met Gly Glu Leu Glu Pro Ser Glu Gly
465                     470                 475                 480

Lys Ile Lys His Ser Gly Arg Ile Ser Phe Cys Ser Gln Phe Ser Trp
                    485                 490                 495

Ile Met Pro Gly Thr Ile Lys Glu Asn Ile Ile Phe Gly Val Ser Tyr
                    500                 505                 510

Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Ile Val Leu Gly Glu Gly
            530                 535                 540

Gly Ile Thr Leu Ser Gly Gly Gln Arg Ala Arg Ile Ser Leu Ala Arg
545                     550                 555                 560

Ala Val Tyr Lys Asp Ala Asp Leu Tyr Leu Leu Asp Ser Pro Phe Gly
                    565                 570                 575

Tyr Leu Asp Val Leu Thr Glu Lys Glu Ile Phe Glu Ser Cys Val Cys
                    580                 585                 590

Lys Leu Met Ala Asn Lys Thr Arg Ile Leu Val Thr Ser Lys Met Glu
            595                 600                 605

His Leu Lys Lys Ala Asp Lys Ile Leu Ile Leu His Glu Gly Ser Ser
            610                 615                 620

Tyr Phe Tyr Gly Thr Phe Ser Glu Leu Gln Asn Leu Gln Pro Asp Phe
625                     630                 635                 640

Ser Ser Lys Leu Met Gly Cys Asp Ser Phe Asp Gln Phe Ser Ala Glu
                    645                 650                 655
```

-continued

```
Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
            755                 760                 765

Val Leu Asn Leu Met Thr His Ser Val Asn Gln Gly Gln Asn Ile His
770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Leu Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
            915                 920                 925

Met Gly Phe Phe Arg Gly Leu Pro Leu Val His Thr Leu Ile Thr Val
930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
            995                 1000                1005

Ala Val Leu Gln Pro Tyr Ile Phe Val Ala Thr Val Pro Val Ile Val
    1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
                1045                1050                1055

Thr Ser Leu Lys Gly Leu Trp Thr Leu Arg Ala Phe Gly Arg Gln Pro
            1060                1065                1070
```

-continued

```
Tyr Phe Glu Thr Leu Phe His Lys Ala Leu Asn Leu His Thr Ala Asn
    1075                1080                1085

Trp Phe Leu Tyr Leu Ser Thr Leu Arg Trp Phe Gln Met Arg Ile Glu
    1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
                1125                1130                1135

Met Asn Ile Met Ser Thr Leu Gln Trp Ala Val Asn Ser Ser Ile Asp
            1140                1145                1150

Val Asp Ser Leu Met Arg Ser Val Ser Arg Val Phe Lys Phe Ile Asp
            1155                1160                1165

Met Pro Thr Glu Gly Lys Pro Thr Lys Ser Thr Lys Pro Tyr Lys Asn
            1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
                1205                1210                1215

Ala Lys Tyr Thr Glu Gly Gly Asn Ala Ile Leu Glu Asn Ile Ser Phe
            1220                1225                1230

Ser Ile Ser Pro Gly Gln Arg Val Gly Leu Leu Gly Arg Thr Gly Ser
            1235                1240                1245

Gly Lys Ser Thr Leu Leu Ser Ala Phe Leu Arg Leu Leu Asn Thr Glu
    1250                1255                1260

Gly Glu Ile Gln Ile Asp Gly Val Ser Trp Asp Ser Ile Thr Leu Gln
1265                1270                1275                1280

Gln Trp Arg Lys Ala Phe Gly Val Ile Pro Gln Lys Val Phe Ile Phe
            1285                1290                1295

Ser Gly Thr Phe Arg Lys Asn Leu Asp Pro Tyr Glu Gln Trp Ser Asp
            1300                1305                1310

Gln Glu Ile Trp Lys Val Ala Asp Glu Val Gly Leu Arg Ser Val Ile
            1315                1320                1325

Glu Gln Phe Pro Gly Lys Leu Asp Phe Val Leu Val Asp Gly Gly Cys
    1330                1335                1340

Val Leu Ser His Gly His Lys Gln Leu Met Cys Leu Ala Arg Ser Val
1345                1350                1355                1360

Leu Ser Lys Ala Lys Ile Leu Leu Leu Asp Glu Pro Ser Ala His Leu
            1365                1370                1375

Asp Pro Val Thr Tyr Gln Ile Ile Arg Arg Thr Leu Lys Gln Ala Phe
            1380                1385                1390

Ala Asp Cys Thr Val Ile Leu Cys Glu His Arg Ile Glu Ala Met Leu
            1395                1400                1405

Glu Cys Gln Gln Phe Leu Val Ile Glu Glu Asn Lys Val Arg Gln Tyr
    1410                1415                1420

Asp Ser Ile Gln Lys Leu Leu Asn Glu Arg Ser Leu Phe Arg Gln Ala
1425                1430                1435                1440

Ile Ser Pro Ser Asp Arg Val Lys Leu Phe Pro His Arg Asn Ser Ser
                1445                1450                1455

Lys Cys Lys Ser Lys Pro Gln Ile Ala Ala Leu Lys Glu Glu Thr Glu
            1460                1465                1470

Glu Glu Val Gln Asp Thr Arg Leu
    1475                1480
```

ANTIBODIES SPECIFIC FOR CYSTIC FIBROSIS TRANSMEMBRANE CONDUCTANCE REGULATOR AND USES THEREFOR

RELATED APPLICATIONS

This application is a continuation of application Ser. No. 08/114,950, filed Aug. 27, 1993, now abandoned, which is a continuation-in-part application of U.S. Ser. No. 08/087,132 filed Jul. 2, 1993, which is a continuation application of U.S. Ser. No. 07/613,592, filed Nov. 15, 1990, now abandoned, which is in turn a continuation-in-part application of U.S. Ser. No. 07/589,295 filed Sep. 27, 1990, now abandoned, which is a continuation-in-part application of U.S. Ser. No. 07/488,307, filed Mar. 5, 1990, now abandoned. This application is also related to the subject matter described in application U.S. Ser. No. 07/985,478 filed Dec. 2, 1992, now abandoned. The contents of all of the above co-pending patent applications are incorporated herein by reference. Definitions of language or terms not provided in the present application are the same as those set forth in the copending applications. Any reagents or materials used in the examples of the present application whose source is not expressly identified also is the same as those described in the copending application, e.g., ΔF508 CFTR gene and CFTR antibodies.

BACKGROUND OF THE INVENTION

Cystic Fibrosis (CF) is the most common fatal genetic disease in humans (Boat, T. et al. Cystic fibrosis. In: *The Metabolic Basis of Inherited Disease*, C. Scriver, A. Beaudet, W. Sly, and D. Valle, eds. (McGraw Hill, New York, 1989), 2649–2860). Based on both genetic and molecular analysis, a gene associated with CF was isolated as part of 21 individual cDNA clones and its protein product predicted (Kerem, B-S. et al. *Science* 245:1073–1080 (1989); Riordan, J. et al. *Science* 245:1066–1073 (1989); Rommens, J. H. et al. *Science* 245:1059–1065 (1989)).

U.S. Ser. No. 07/488,307, filed Mar. 5, 1990, and now abandoned, describes the construction of the gene into a continuous strand, expression of the gene as a functional protein and confirmation that mutations of the gene are responsible for CF. (See also Gregory, R. J. et al. *Nature* 347:382–386 (1990); Rich, D. P. et al. *Nature* 347:358–363 (1990)). The copending patent application also discloses experiments which showed that proteins expressed from wild type but not a mutant version of the cDNA complemented the defect in the cAMP regulated chloride channel shown previously to be characteristic of CF.

The protein product of the CF associated gene is called the cystic fibrosis transmembrane conductance regulator (CFTR) (Riordan, J. et al. *Science* 245:1066–1073 (1989)). CFTR is a protein of approximately 1480 amino acids made up of two repeated elements, each having six transmembrane segments and a nucleotide binding domain. The two repeats are separated by a large, polar, so-called R-domain containing multiple potential phosphorylation sites. Based on its predicted domain structure, CFTR is a member of a class of related proteins which includes the multi-drug resistant (MDR) P-glycoprotein, bovine adenyl cyclase, the yeast STE6 protein as well as several bacterial amino acid transport proteins (Riordan, J. et al. *Science* 245:1066–1073 (1989); Hyde, S. C. et al. *Nature* 346:362–365 (1990)). Proteins in this group, characteristically, are involved in pumping molecules into or out of cells.

CFTR has been postulated to regulate the outward flow of anions from epithelial cells in response to phosphorylation by cyclic AMP-dependent protein kinase or protein kinase C (Riordan, J. et al. *Science* 245:1066–1073 (1989); Frizzell, R. A. et al. *Science* 233:558–560 (1986); Welsh, M. J. and Liedtke, C. M. *Nature* 322:467 (1986); Li, M. et al. *Nature* 331:358–360 (1988); Hwang, T-C. et al. *Science* 244;1351–1353 (1989); Li, M. et al. *Science* 244:1353–1356 (1989)).

SUMMARY OF THE INVENTION

In order to clarify the role of cystic fibrosis transmembrane conductance regulator (CFTR) in cystic fibrosis, further study of the CFTR molecule is needed. The availability of antibodies which bind to defined epitopes which have different locations on the CFTR molecule would greatly facilitate the characterization of the CFTR molecule. In addition, such antibodies would aid in the efficient purification of CFTR from an impure solution and detection of CFTR in biological samples containing CFTR.

The present invention pertains to antibodies which bind to epitopes of CFTR. The antibodies of the present invention can be monoclonal or polyclonal antibodies which are preferably raised against human cystic fibrosis transmembrane conductance regulator. The present invention also pertains to hybridomas producing antibodies, such as mAb 13-1, mAb 13-2, mAb 24-1, and mAb 24-2, which bind to an epitope of CFTR.

The present invention further pertains to a method of purifying CFTR from an impure solution containing CFTR. The method involves contacting the impure solution with an antibody which binds an epitope of CFTR, allowing the antibody to bind to CFTR to form an immunological complex, and separating the complex from the impure solution. The method of purification can further comprise separating the CFTR from the antibody and recovering the CFTR. In one embodiment, the separation is conducted by contacting the immunological complex with a saturating amount of peptide comprising the epitope recognized by the antibody of the immunological complex.

The present invention still further pertains to a method for detecting CFTR in a biological sample. The method involves contacting the biological sample with an antibody which binds an epitope of CFTR, allowing the antibody to bind to CFTR to form an immunological complex, and detecting the formation of the immunological complex and correlating presence or absence of the immunological complex with presence or absence of CFTR in the biological sample.

Another aspect of the present invention is a method for detecting human cystic fibrosis transmembrane regulator in a biological sample from a nonhuman cystic fibrosis knockout animal wherein the nonhuman cystic fibrosis knockout animal has been subjected to human CFTR replacement therapy. The method involves contacting the biological sample with an antibody which binds an epitope of human CFTR which is different from the corresponding CFTR amino acid sequence in the nonhuman cystic fibrosis knockout animal, allowing the antibody to bind to the human CFTR to form an immunological complex, and detecting the formation of the immunological complex and correlating the presence or absence of the complex with presence or absence of human CFTR.

Still another aspect of the present invention is a method for determining the orientation of CFTR in the membrane of a lipid vesicle. The method includes contacting the lipid vesicle with an antibody which binds to a selected surface epitope of CFTR, such as an extracellular or an intracellular surface epitope, allowing the antibody to bind to CFTR to form an immunological complex, and detecting the formation of the immunological complex and correlating presence or absence of the immunological complex with correct or incorrect orientation of the CFTR in the membrane of the lipid vesicle.

Yet another aspect of the present invention is a kit for detecting CFTR in a biological sample. The kit includes a container holding an antibody which binds to an epitope of CFTR and instructions for using the antibody for the purpose of binding to CFTR to form an immunological complex and detecting the formation of the immunological complex such that presence or absence of the immunological complex correlates with presence or absence of CFTR.

DETAILED DESCRIPTION

Figure 1:
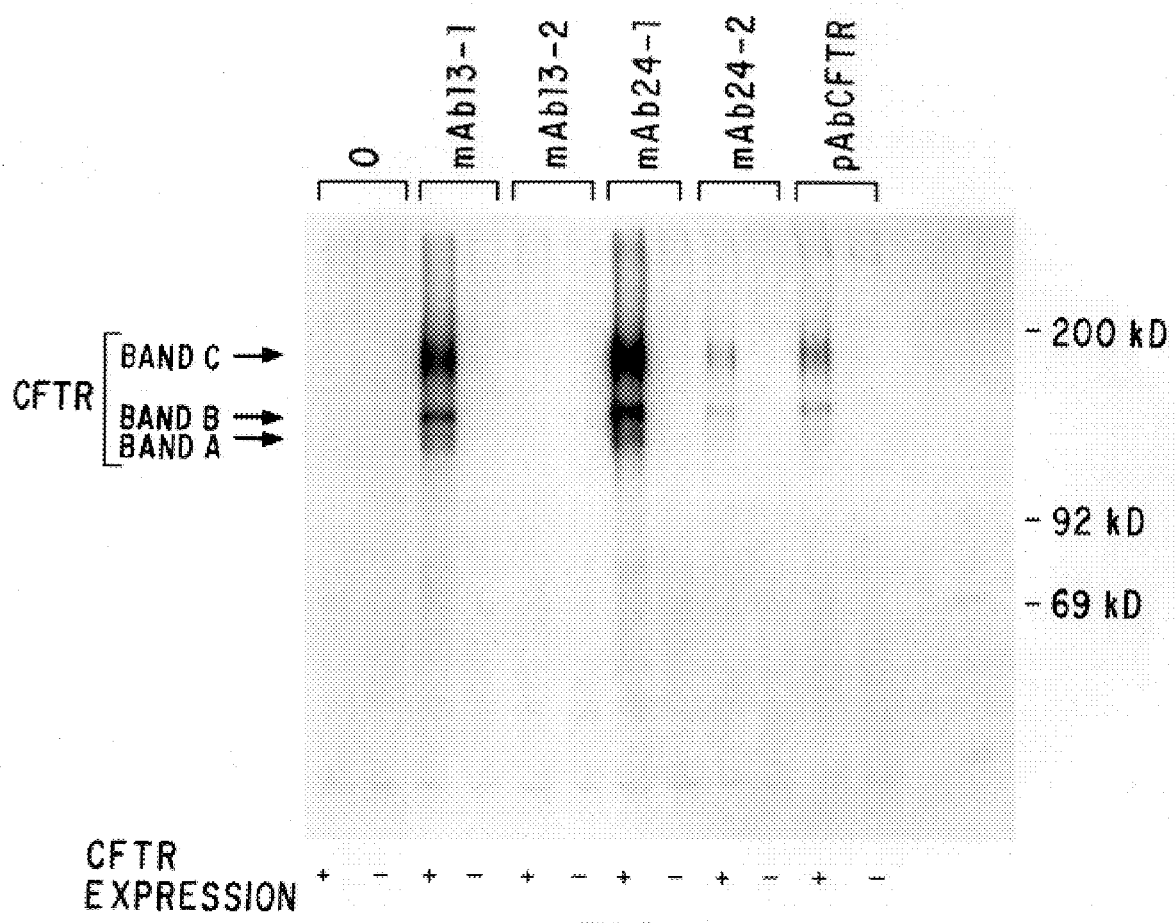
FIG. 1 depicts an autoradiograph of a gel showing immunoprecipitation of CFTR by monoclonal antibody mAb 13-1, monoclonal antibody mAb 24-1, monoclonal antibody mAb 24-2, and polyclonal antibody pAb CFTR.

The present invention provides antibodies which bind to epitopes of cystic fibrosis transmembrane conductance regulator (CFTR). These antibodies can be used to purify CFTR from an impure solution containing CFTR, to detect CFTR in by a biological sample, and to determine the orientation of CFTR in the membrane of a lipid vesicle. In addition, the antibodies can be used in kits for detecting CFTR in a biological sample.

The term "antibody" is art-recognized terminology and is intended to include molecules or active fragments of molecules that bind to known antigens. Examples of active fragments of molecules that bind to known antigens include Fab and F(ab')$_2$ fragments. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. *J. Nucl. Med.* 23:1011–1019 (1982). The term "antibody" also includes bispecific and chimeric antibodies.

The language "monoclonal antibody" is art-recognized terminology. The monoclonal antibodies of the present invention can be prepared using classical cloning and cell fusion techniques. The immunogen (antigen) of interest, e.g. different portions of CFTR, is typically administered (e.g. intraperitoneal injection) to mice or rabbits as a fusion protein to induce an immune response. Fusion proteins comprise the peptide against which an immune response is desired coupled to carrier proteins, such as β-galactosidase, glutathione S-transferase, keyhole limpet hemocyanin (KLH), and bovine serum albumin. In these cases, the peptides serve as haptens with the carrier proteins. After the mouse or rabbit is boosted, for example, three or four times, the spleen is removed and splenocytes are extracted and fused with myeloma cells using the well-known processes of Kohler and Milstein (*Nature* 256: 495–497 (1975)) and Harlow and Lane (Antibodies: A Laboratory Manual (Cold Spring Harbor Laboratory, New York 1988)). The resulting hybrid cells are then cloned in the conventional manner, e.g. using limiting dilution, and the resulting clones, which produce the desired monoclonal antibodies, cultured.

Examples of monoclonal antibodies raised against human CFTR using this method include mAb 13-1, mAb 13-2, mAb 24-1, and mAb 24-2. The monoclonal antibodies mAb 13-1 and mAb 13-2 recognize amino acids found in exon 13. MAb 13-1, for example, recognizes amino acids 729–736 of human CFTR and is produced by the hybridoma deposited under American Type Culture Collection (ATCC) Accession No. ATCC HB 10565. MAb 13-2 is produced by the hybridoma deposited under ATCC Accession No. HB 10566. Because the sequence of human CFTR (SEQ ID NO:1 and SEQ ID NO:2, which correspond to the nucleic acid sequence encoding CFTR and the amino acid sequence of CFTR published in Riordan, J. R. et al. *Science* 245:1066–1073 (September 1989)) recognized by mAb 13-1 is different from the corresponding sequence of mouse CFTR, it is predicted that mAb 13-1 will not recognize the mouse form of CFTR. This characteristic of mAb 13-1 can be useful in testing for gene or protein transfer of human CFTR into cystic fibrosis "knockout" mice. See Dorin, J. R. et al. *Nature* 359:211–216 (September 1992); Colledge, W. H. et al. *The Lancet* 340:680 (September 1992); Snouwaert, J. N. et al. *Science* 257:1083–1088 (August 1992) for examples of mouse models for cystic fibrosis. MAb 24-1 recognizes amino acids 1477–1480 of human CFTR and is produced by the hybridoma deposited under ATCC Accession No. ATCC HB11947. Because the sequence recognized by mAb 24-1 comprises the last four amino acids of human CFTR, the antibody can be used as a probe for the full length CFTR. For example, mAb 24-1 will not recognize CFTR lacking just the carboxy terminal amino acid. Like mAb 13-1, mAb 24-1 does not recognize mouse CFTR and is likewise useful in testing for gene or protein transfer of human CFTR into cystic fibrosis "knockout" mice. MAb 24-2 recognizes amino acids 1433–1439 of human CFTR and is produced by the hybridoma deposited under ATCC Accession No. ATCC HB11946. As with mAb 13-1 and mAb 24-1, mAb 24-2 does not recognize mouse CFTR and can be used in cystic fibrosis mouse "knockout" models for testing gene or protein transfer of human CFTR.

The language "polyclonal antibody" is art-recognized terminology. Examples of polyclonal antibodies raised against human CFTR include pAb ECL1-18, pAb ECL1-12, and pAb CFTR. The immunogen used to produce pAb ECL1-18 was a peptide comprising amino acids 102–119 of human CFTR coupled to the carrier keyhole limpet hemocyanin. The epitopes recognized by pAb ECL1-18 comprise amino acids 103–119 which are predicted to lie on the extracellular surface of the CFTR molecule. These antibodies are, therefore, useful for studying the topology of CFTR. In addition, these antibodies can be used to determine the orientation of CFTR reconstituted into artificial liposomes or virosomes. The separation of correctly-oriented from incorrectly-oriented liposomes or virosomes can be achieved using affinity chromatography. Anholt et al. *J. Biol. Chem.* 256:4377 (1981). The immunogen used to produce pAb ECL1-12 was a peptide comprising amino acids 106–117 of human CFTR, amino acids also predicted to lie on the extracellular surface of the CFTR molecule. The immunogen used to produce pAb CFTR was the entire human CFTR protein purified from insect cells. See George et al. *Biochem. Biophys. Res. Comm.* 163:1265 (1989) for an example of a system used to express a membrane protein in insect cells. Because its epitopes (over 40) span the entire CFTR, it is likely a useful antibody for immunoprecipitation experiments. In addition, it is likely to cross-react with CFTRs of all species.

A common method for preparing polyclonal antibodies to an immunogen of interest, such as CFTR or a fragment thereof, includes injecting (e.g. intradermally, intramuscularly) an animal, such as a rabbit, with an the immunogen emulsified in Freund's complete adjuvant. This process is repeated after two weeks. Two weeks later, monthly subcutaneous booster injections can begin with the immunogen in Freund's incomplete adjuvant. The animals are bled biweekly by a marginal ear vein technique beginning six weeks after the primary immunization. The collected blood is refrigerated, allowing clots to form, and the supernatant (antiserum) retained.

The term "epitope" is art-recognized. It is generally understood by those of skill in the art to refer to the region of an antigen, such as CFTR, that interacts with an antibody. An epitope of a peptide or protein antigen can be formed by contiguous or noncontinguous amino acid sequences of the antigen. CFTR, like many large proteins, contains many epitopes. Examples of human CFTR epitopes recognized by antibodies of the present invention include the amino acid sequences 729–736, Asp-Glu-Pro-Leu-Glu-Arg-Arg-Leu (SEQ ID NO:2); 1477–1480, Asp-Thr-Arg-Leu (SEQ ID NO:2); and 1433–1439, Glu-Arg-Ser-Leu-Phe-Arg-Gln (SEQ ID NO:2). These peptides offer a convenient method for eluting CFTR bound to either mAb 13-1, mAb 13-2, mAb 24-1, and mAb 24-2 on immunoaffinity columns. For example, when an antibody which recognizes the epitope for either mAb 13-1, mAb 24-1, or mAb 24-2, is used in an immunoaffinity column to purify CFTR, the peptide recognized by the antibody can be added to the immunoaffinity column to elute the CFTR. See below for a more detailed description of the purification of CFTR.

The language "cystic fibrosis transmembrane conductance regulator" is intended to include wild-type cystic fibrosis transmembrane conductance regulator and mutant cystic fibrosis transmembrane conductance regulator. The sequences of the DNA encoding the human wild-type cystic fibrosis transmembrane conductance regulator and the DNA encoding the mutant cystic fibrosis transmembrane conductance regulator were described previously in the copending applications identified under the Related Applications section. Mutant CFTRs include proteins having mutations introduced at residues known to be altered in CF chromosomes (ΔG508, ΔI507, R334W, S5491, G551D) and at residues believed to play an important role in the function of CFTR (e.g., K464N, F508R, N894, 900Q, K1250M). See Example 7 of U.S. Ser. No. 07/935,603, filed Aug. 26, 1992, now abandoned. See Tsui, L-C *Trends in Genetics* 8(11) :392–398 (November, 1992) for additional examples of the approximately 300 sequence alterations of CFTR identified to date.

The language "extracellular surface" is intended to include regions of a protein, such as CFTR, that extend into the extracellular space. For example, it has been predicted that amino acids 103–119 of CFTR lie on the extracellular surface. The language "intracellular surface" is intended to include regions of a protein, such as CFTR, that extend into the intracellular space. For example, the amino acids that comprise the nucleotide-binding domain of CFTR as well as the R-domain lie on the intracellular surface of CFTR.

The language "carboxy terminus" is intended to include amino acids located at the carboxy terminal portion of an antigen. For example, 50% of the amino acids on an antigen lie on the carboxy side of the molecule and are intended to be included in this definition. CFTR is a protein of approximately 1480 amino acids. Carboxy terminal amino acids of CFTR include amino acids 741–1480. The antibody mAb 24-1 of the present invention was raised against the CFTR carboxy terminal amino acids 1477–1480.

The present invention also pertains to hybridomas producing antibodies which bind to an epitope of cystic fibrosis transmembrane conductance regulator. The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and Example 1 below for a more detailed description of the method of fusion. The hybridoma which produces mAb 13-1 is deposited under ATCC Accession Number HB 10565. The hybridoma which produces mAb 13-2 is deposited under ATCC Accession Number HB 10566. The hybridoma which produces mAb 24-1 is deposited under ATCC Accession Number HB11947. The hybridoma which produces mAb 24-2 is deposited under ATCC Accession Number HB11946.

The present invention further pertains to a method for purifying CFTR from an impure solution containing CFTR. The method involves contacting the impure solution with an antibody which binds an epitope of CFTR, allowing the antibody to form an immunological complex, and separating the complex from the impure solution. The method of purification can further comprise separating the CFTR from the antibody and recovering the CFTR. In one embodiment, the separation is conducted by contacting the immunological complex with a saturating amount of peptide comprising the epitope recognized by the antibody of the immunological complex.

The term "purifying" is intended to include removal of unwanted constituents of an impure solution containing CFTR such that the concentration of CFTR in the solution after purification is greater that the concentration of CFTR in the solution prior to purification and the concentration of at least one unwanted constituent in the solution after purification is less than the concentration of the unwanted constituent in the solution prior to purification. Unwanted constituents include molecules other than CFTR. It should be understood that the extent of the purification of the solution can depend on the intended use of the CFTR. For example, the CFTR purified for therapeutic use will have to be more pure than CFTR purified for research purposes.

The language "impure solution" is intended to include a mixture of compounds which includes CFTR and at least one non-CFTR compound. For example, an impure solution can comprise a biological sample containing CFTR as defined below. Alternatively, an impure solution can comprise cell homogenates of cells that contain CFTR. Cell homogenates typically contain the components of the cell culture medium as well as disrupted cellular components, e.g. cellular macromolecules, such as CFTR, organelles, lysosomes. Because CFTR is a membrane protein, it is important to accomplish solubilization of CFTR from its native membrane such as by using detergents. In this case, the cell homogenate containing CFTR is generated by first determining conditions for solubilization of CFTR from its natural lipid environment using whole cells or membrane preparations prepared from cells. The initial solubilization experiments will involve screening a variety of detergents at varying concentrations in order to find conditions that preferably achieve maximal solubilization of CFTR. Briefly, packed membrane pellets are resuspended in detergent solution, gently homogenized, and the insoluble material removed by centrifugation at 100,000 g for one hour. The degree of solubilization achieved is ideally monitored immunologically. Potential detergents include, but are not limited to, CHAPS (3-{3-choamidopropyl) dimethylammonio}-1-pro(anesulfonate) (Borsotto, M. et al. *J. Biol. Chem.* 260:14255 (1985); Hamada and Tsuro, *J.*

*Biol. Chem.* 263:1454 (1988)), n-octyl glucoside (Landry et al. *Science* 244:1469 (1989), lubrol (Smigel, *J. Biol. Chem.* 261:1976 (1986); Agnew et al. *BBRC* 92:860 (1980)), Triton X-100 (Hartshorne and Catterall, *J. Biol. Chem.* 259:1667 (1984), and Triton X-114 (Bordier, *J. Biol. Chem.* 256:1604 (1981)). The initial detergent solubilized CFTR solution can also be diluted into an appropriate concentration of detergent or detergent/lipid (Agnew and Raftery, *Biochemistry* 18:1912 (1979)) to achieve stabilization of the CFTR. Compounds known to stabilize proper folding of membrane proteins sometimes referred to as ozmolytes can also be used. These include polyols such as glycerol, sugars, and amino acids (Ambudkar and Maloney, *J. Biol. Chem.* 261:10079 (1986)). In addition, protease inhibitors against the four major classes of proteases can be advantageously made present throughout these procedures (Hartshorne and Catterall, *J. Biol. Chem.* 259:1667 (1984)) and these would include, for example, phenylmethylsulfonyl fluoride for serine proteases, iodoacetaminde for thiol proteases, 1,10-phenanthroline for metalloproteases, and pepstatin A for proteases with activated carboxylic acid groups. Ideally, studies should be carried out in which the concentrations and relative proportions of detergent, lipid, and ozmolyte are varied together with other buffer conditions in order to identify optimal conditions to preserve and stabilize the CFTR. For example, Agnew and Rafferty, supra, varied the ratio of various detergents and lipids and determined that a 7 to 1 ratio of lubrol to phosphatidylcholine stabilized the solubilized voltage sensitive sodium channel for further purification. Similarly, Hartshorne and Catterall, supra, found that the presence of 0.25% egg phosphatidylcholine produced a more stable preparation and an increased recovery during purification of the sodium channel solubilized with Triton X-100. To determine the functional integrity of the solubilized protein may require reconstitution of the protein into liposomes. See Example 11 of U.S. Ser. No. 07/589,295, filed Sep. 27, 1990.

In addition, an impure solution can comprise culture media which has been used to culture cells containing CFTR and, therefore, can contain CFTR. Examples of cultured cells that normally contain CFTR include immortalized airway epithelial cells (e.g. nasal and lung epithelial cells) from cystic fibrosis victims. Examples of cells which do not normally contain CFTR but can be engineered to express CFTR include 3T3 fibroblasts, C127, and COS-7 cells. These cells can be transfected with nucleic acid which encodes and directs expression of CFTR.

The language "immunological complex" is intended to include an antigen, such as CFTR or a fragment thereof, bound to an antibody, such as a monoclonal or polyclonal antibody, or a fragment thereof. The antigen and antibody are typically bound to one another through noncovalent interactions.

The immunological complex as well as the antigen alone can be separated from the impure solution by any separation technique known to those of ordinary skill in the art. For example, one commonly used separation method is immunoaffinity chromatography. See Harlow and Lane, Antibodies: A Laboratory Manual (Cold Spring Harbor Laboratory, New York 1988) 511–552. Immunoaffinity purification generally consists of three steps: preparation of an antibody-matrix, binding of an antigen to the antibody-matrix, and elution of the antigen. In the first step, either monoclonal antibodies or affinity-purified polyclonal antibodies can be covalently attached to a solid-phase matrix. An example of covalent attachment of the antibody to the solid-phase matrix is linkage of the antibody to protein A beads. See Harlow and Lane, Antibodies: A Laboratory Manual (Cold Spring Harbor Laboratory, New York 1988) 521–523. After the preparation of the antibody-solid phase matrix, the antigen is bound to the antibody and contaminating molecules are removed by washing. In the final step, the antigen-antibody interaction is broken by treating the immune complexes with strong elution conditions, adding a saturating amount of a small compound (e.g. the peptide comprising the epitope recognized by the antibody used in the column) that mimics the binding site, and/or treating with an agent which induces an allosteric change that releases the antigen, to release the antigen into the eluate. Optimal conditions for binding the antigen to the column, washing the column to remove contaminants, and eluting the purified antigen can be determined using conventional parameters as the starting point and testing the effect of varying the parameters. It is recognized that effective wash and elution conditions will significantly impact the degree of purification obtained. Extensive washing in the presence of stabilizers plus higher salt and differing detergents can be utilized to remove nonspecifically adsorbed proteins. Elution can then be carried out most advantageously by lowering the pH followed by immediate pH neutralization of the eluted fractions, by using the above-described specific peptide elution (Courtneige et al. Cold Spring Harbor Conference on Cell Prolif. and Cancer 2:123 (1984)), or chaotropic agents such as potassium thiocyanate.

Although it is likely that immunoaffinity chromatography would provide a significant purification and provide protein of sufficient purity for research studies and drug screening, such an approach alone may not provide adequate protein purity to qualify CFTR as a clinical grade therapeutic agent. Thus, to purify the protein further, or in the case that immunoaffinity chromatography was unsuccessful, one could test a number of additional chromatographic approaches to select an optimal chromatography procedure to obtain the desired purity. For example, ligand affinity (Landry et al. *Science* 244:1469 (1989); Smigel, *J. Biol. Chem.* 261:1976 (1986)), lectin (Curtis and Catterall, *Biochemistry* 23:2113 (1984)), anion exchange (Hartshorne and Catterall, *Proc. Natl. Acad. Sci. USA* 78:4620 (1981)) hydroxyapatite (Hartshorne and Catterall, *J. Biol. Chem.* 259:1667 (1984)), and gel filtration (Borsotto et al. *J. Biol. Chem.* 260:14255 (1985)) chromatographic procedures have been used in purification schemes for this class of membrane-bound proteins. Since CFTR appears to contain a nucleotide binding domain, it may bind to resins such as Cibicron blue and be specifically eluted with nucleotides (Lowe and Pearson, *Methods in Enzymology* 104:97 (1984)). The accessibility of the nucleotide binding domain in the solubilized form would have to be determined empirically. The amino acid sequence of CFTR contains carbohydrate attachment sites at amino acids 894 and 900. It has also been shown that CFTR is a glycoprotein. Cheng, S. H. et al. *Cell* 63:827–834 (November 1990). Thus, lectin chromatography can be used to purify CFTR.

The present invention still further pertains to a method for detecting CFTR in a biological sample containing CFTR. The method includes contacting the biological sample with an antibody which binds an epitope of CFTR, allowing the antibody to bind to CFTR to form an immunological complex, and detecting the formation of the immunological complex and correlating presence or absence of the immunological complex with presence or absence of CFTR in the biological sample.

The language "detecting the formation of the immunological complex" is intended to include discovery of the presence or absence of CFTR in a biological sample. The presence or absence of CFTR can be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York 1988) 555–612. Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies.

The language "biological sample" is intended to include biological material, e.g. cells, tissues, or biological fluid which, as it exists in nature, contains CFTR, e.g. sputum from cystic fibrosis victims, biological material that does not contain CFTR as it exists in nature but can be engineered to contain CFTR (e.g. cells, tissues) or contains CFTR as a result of its proximity to biological material (e.g. biological fluids from the extracellular space adjacent to cells which naturally contain CFTR or cells that have been engineered to contain CFTR) that naturally contains CFTR or has been engineered to express CFTR, or biological material which has been subjected to CFTR replacement therapy. Biological material, such as cells, can be engineered to contain CFTR by transfection with nucleic acid which encodes and directs expression of CFTR. For example, an adenovirus-based gene therapy vector the Ela and Elb regions of the genome of which have been deleted and replaced with CFTR-encoding nucleic acid can be used to deliver nucleic acid encoding CFTR to airway epithelial cells in vivo. See U.S. Ser. No. 07/985,478, filed Dec. 2, 1992. Another example of CFTR replacement therapy involves delivering CFTR directly to cells containing defective CFTR. See Example 8 of U.S. Ser. No. 08/087,132, filed Jul. 2, 1993, now abandoned.

Another aspect of the present invention is a method for detecting human CFTR in a biological sample from a nonhuman cystic fibrosis knockout animal having been subjected to human CFTR replacement therapy. The method involves contacting the biological sample with an antibody which binds an epitope of human CFTR which is different from the corresponding CFTR amino acid sequence in the nonhuman cystic fibrosis knockout animal, allowing the antibody to bind to the human CFTR to form an immunological complex, and detecting the formation of the immunological complex and correlating presence or absence of the immunological complex with presence or absence of human CFTR.

The language "nonhuman cystic fibrosis knockout animal" is intended to include a nonhuman animal the CFTR gene of which is disrupted or altered such that the animal displays at least one feature common to human cystic fibrosis patients, such as excess mucus in the lungs, intestinal obstruction, or reduced ability to digest and absorb duodenal contents because of pancreatic insufficiency. Examples of nonhuman animals in which the CFTR gene can be disrupted or altered include nonhuman animals that contain the CFTR gene. One noted example of such an animal is a mouse. Methods for generating cystic fibrosis knockout mice are described in Dorin, J. R. et al. *Nature* 359:211–216 (September 1992) and Snouwaert, J. N. et al. *Science* 257:1083–1088 (August 1992). These cystic fibrosis knockout mice can be used as model systems for the development and testing of therapies for cystic fibrosis patients. These model systems can be used to test targeted gene replacement therapy using, for example, adenovirus-based gene therapy vectors containing nucleic acid encoding functional CFTR. See U.S. Ser. No. 07/985,478, filed Dec. 2, 1992, now abandoned. Alternatively, these model systems can be used to test protein therapy. Protein therapy can be accomplished by using CFTR produced by host cells transformed or transfected with CFTR cDNA to correct the cystic fibrosis defect directly by introducing the protein into the membrane of cells lacking functional CFTR. This approach can augment the defective protein by addition of the wild-type molecule. See Example 8 of U.S. Ser. No. 08/087,132, filed Jul. 2, 1993. Most preferably, treatment of individuals with cystic fibrosis will comprise the administration of a therapeutically effective amount of replacement CFTR. Ideally, the CFTR will be administered via aerosol inhalation so that is applied directly to the airway cells. The CFTR can be formulated in a lipid vesicle, such as in a liposome or in a virosome. The final formulation can advantageously comprise a carrier as a vehicle for physically transporting the CFTR and also ideally chemically stabilizing the CFTR. The most preferred embodiment also can comprise a dissolving agent for dissolving the mucus or otherwise assisting the movement of the CFTR through the mucus layer to the airway cellular membrane. Ideal agents in this regard would target the CFTR and/or the delivery vehicle to airway cells and further, promote fusion therewith.

Still another aspect of the present invention is a method for determining the orientation of CFTR in the membrane of a lipid vesicle. The method includes contacting the lipid vesicle with an antibody which binds to an extracellular surface epitope of CFTR, allowing the antibody to bind to the CFTR to form an immunological complex, and detecting the formation of the immunological complex and correlating presence or absence of the immunological complex with correct or incorrect orientation of the CFTR in the membrane of the lipid vesicle.

The term "orientation" is intended to include the position of CFTR in the membrane of a lipid vesicle. For example, in its functional state in a cell, CFTR is in certain position, e.g. with certain amino acids on the extracellular surface, certain amino acids within the membrane (e.g. transmembrane segments), and other amino acids on the intracellular surface of the molecule (e.g. amino acids comprising the nucleotide binding domain and the R-domain. This is the correct orientation of CFTR within a cellular membrane. In addition, it is the correct orientation of CFTR that has been reconstituted into lipid vesicles. See Example 11 of U.S. Ser. No. 08/087,132, filed Jul. 2, 1993 for a description of the formulation of CFTR into artificial liposomes. The incorrect orientation of CFTR within either a cellular membrane or a membrane of a lipid vesicle is one in which the regions of a functional form of CFTR that are normally in one position are no longer in that position. For example, a functional form of CFTR is in an incorrect orientation in the membrane of a lipid vesicle when the amino acid sequences which are normally on the extracellular surface of the vesicle are no longer on the extracellular surface, e.g., they may be in a transmembrane segment or on the intracellular surface of the vesicle. Antibodies which recognize epitopes which are on the extracellular surface or intracellular surface of a functional form of CFTR in its correct orientation in a membrane can be used to determine the orientation of CFTR when it has been reconstituted in a membrane of a lipid vesicle. The separation of correctly-oriented from incorrectly-oriented lipid vesicles can be accomplished using affinity chromatography. Anholt et al. *J. Biol. Chem.* 256:4377 (1981). The language "lipid vesicle" is intended to include a lipid membrane-bound compartment. Examples of lipid vesicles include liposomes, microsomes, and virosomes.

Yet another aspect of the present invention is a kit for detecting CFTR in a biological sample containing CFTR. The kit includes a container holding an antibody which binds an epitope of CFTR and instructions for using the antibody for the purpose of binding to CFTR to form an immunological complex and detecting the formation of the immunological complex such that the presence or absence of the immunological complex correlates with presence or absence of CFTR. Examples of containers include multiwell plates which allow simultaneous detection of CFTR in multiple samples.

The present invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Example 1
Preparation of Monoclonal Antibodies mAb 13-1, mAb 24-1, and mAb 24-2

Monoclonal antibodies mAb 13-1, mAb 24-1, and mAb 24-2, specific for predetermined regions or epitopes of the CFTR protein, were prepared using classical cloning and cell fusion techniques. The immunogen used to produce the monoclonal antibodies mAb 13-1 and mAb 13-2 was a fusion protein comprising amino acids 591–829 (from exon 13) of the human CFTR and β-galactosidase. The immunogen used to produce mAb 24-1 was a fusion protein comprising glutathione S-transferase and amino acids 1377–1480 of human CFTR. The immunogen used to produce mAb 24-2 was a fusion protein comprising glutathione S-transferase and amino acids 1377–1480 of human CFTR. The fusion proteins were obtained as described in Mole and Lane, DNA Cloning Volume III: A Practical Approach (1987), and used to induce an immune response in a mouse.

For production of monoclonal antibodies mAb 13-1 and mAb 13-2, a suitable immunization procedure is as follows. The immunization procedure required injecting a mouse with 10 micrograms of immunogen in 10 microliters of PBS emulsified in 30 microliters of Freunds complete adjuvant (Gibco # 660-5721 AS). This procedure was repeated four times at intervals of from 1 to 28 days over a 57 day period. The mouse was then injected with 50 micrograms of immunogen in 50 microliters of PBS four times over a three day period. Vasodilation was induced by warming the mouse for 10 minutes with a desk lamp. The mouse was sacrificed by $CO_2$ intoxication and a splenectomy was performed.

An additional immunization scheme for mice (Balb/c females, 6–10 weeks at start of schedule) was to inject each of three with 10 μg of immunogen (fusion protein or peptide) emulsified in Freund's complete adjuvant (final volume 100–150 μl) intraperitoneally on day 0. This was repeated on days 14, 28, and 56 except that Freund's incomplete adjuvant was substituted for the complete. On day 57, 50 μg of immunogen in PBS (25 μl) was injected intravenously via a tail vein. The mice were sacrificed on day 60 and the spleens taken for fusion.

After immunization was carried out, the B-lymphocytes of the immunized mice were extracted from the spleen and fused with myeloma cells using the well known processes of Kohler and Milstein (*Nature* 256:495–497 (1975)) and Harlow and Lane, Antibodies, A Laboratory Manual, Cold Spring Harbor Laboratory, New York (1988), respectively. The resulting hybrid cells were cloned in the conventional manner, e.g., using limiting dilution, and the resulting clones, which produce the desired monoclonal antibodies, cultured.

The hybridomas producing monoclonal antibody mAb 13-1 the monoclonal antibodies mAb 13-2, the monoclonal antibody mAb 24-1, and the monoclonal antibody mAb 24-2, prepared according to this procedure have been deposited with the ATCC and assigned Accession Numbers ATCC HB 10565, ATCC HB 11947, ATCC HB 10566 and ATCC HB 11946, respectively.

Example 2
Preparation of Polyclonal Antibodies pAb ECL1-18, pAb ECL1-12, and pAb CFTR The peptide immunogens obtained from Multiple Peptide Systems were comprised of the following sequences: (1) amino acids 102–119 (Leu-Gly-Arg-Ile-Ile-Ala-Ser-Tyr-Asp-Pro-Asp-Asn-Lys-Glu-Glu-Arg-Ser-Ile) (used to produce pAb ECL1-18); (2) amino acids 106–117 (Ile-Ala-Ser-Tyr-Asp-Pro-Asp-Asn-Lys-Glu-Glu-Arg) (used to produce pAb ECL1-12); and (3) the entire amino acid sequence 1–1480 of CFTR (SEQ ID NO:2) (used to produce pAb CFTR). Peptide purity as assessed by reverse-phase high-pressure liquid chromatography (HPLC) were judged to be greater than 85% and amino acid composition analysis of the synthetic peptides yielded excellent correspondence between expected and experimental values for all the peptides. The first two peptides were coupled to keyhole limpet hemocyanin (KLH) to increase their antigenicity by utilizing a terminal cysteine residue introduced into all three peptides to facilitate specific coupling to the carrier protein through the thiol moiety using the m-Maleimidobenzoyl-N-hydroxysuccinimide ester (MBS) chemistry (Pierce ImmunoTechnology Catalog and Handbook E-161991) at a ratio of 1:1 (w/w).

For rabbits, the schedule was to immunize each of two (New Zealand White, female) with 100 μg of immunogen emulsified in Freund's complete adjuvant (final volume 400–500 μl) intramuscularly on day 0 which was repeated on days 14 and 35 substituting Freund's incomplete adjuvant for complete for these and all subsequent boosts. Blood was taken (20–30 mls) one, three, and five weeks post injection and the rabbits were reboosted 6 weeks after their previous boost before starting the bleeds cycle again.

Affinity Purification of Polyclonal Antibodies pAb ECL1-18, pAb ECL1-12, and pAb CFTR Affinity purification of the polyclonal antibodies was performed on the antisera following a salting out step. The antisera (~20 mls) was made to 45% ammonium sulfate by addition of a 100% saturated solution under gentle mixing. Following one hour equilibration, the precipitate was centrifuged and the pellet washed twice in 50% ammonium sulfate. The final pellet was resuspended in 15 mls PBS and diafiltrated using a Centricon 100 (Amicon, Beverly, Mass.) yielding 0.5 ml–1 ml of antisera enriched for immunoglobulins. The enriched antisera was then loaded directly onto the affinity resin.

The affinity columns used for the peptide antisera were generated by coupling 10 mg of peptide through the terminal cysteine to an activated thiol resin (Immunopure kit #2, Pierce, Rockford, Ill.). The antisera was passed over the column. Non-specific proteins were washed away and the specifically bound antibodies were eluted with 0.1M glycine (pH 2.8) and diafiltrated against PBS.

Biochemical Characterization of Antibodies

Cross-reactivity with CFTR was determined by an immunoprecipitation followed by phosphorylation of CFTR by protein kinase A (IP/PKA) assay. Gregory, R. J. et al. *Nature* 347:6291 (September 1990). Briefly, a recombinant cell-line expressing CFTR (COS-7 cells) is lysed in a 1% Nonidet P40 lysis buffer and cell debris removed by centrifugation. The lysate is made to 1× RIPA (0.1% SDS, 1% Deoxycholate, 1% Triton X-100, 150 mM NaCl, 50mM Tris-HCl pH 8.0) and approximately 1 µg of the test antibody is added. The immune complex is allowed to form for one hour at 4° C. before capture with Pansorbin (Calbiochem, LaJolla, Calif.) precoated with rabbit anti-mouse Igs (Cappel) for thirty minutes. The washed pellet was resuspended in 50 µl of PKA buffer (50 mM Tris-HCl pH 7.5, 10 mM MgCl, BSA 0.1 mg/ml, protein kinase A (Sigma, St. Louis, Mo.), 100 U/ml $^{32}$P-ATP 20 µCI/ml) and incubated at 30° C. for one hour. The Pansorbin pellet was washed and the eluted immunoprecipitate was loaded onto a 6% polyacrylamide gel. Any reaction was visualized by autoradiography. FIG. 1 depicts an autoradiograph of a gel showing immunoprecipitation of CFTR with mAb 13-1 (lane 3), mAb 13-2 (lane 5) mAb 24-1 (lane 7), mAb 24-2 (lane 9), and pAb CFTR (lane 11). Lanes 1 and 2 are controls in which no antibody was incubated with the cell lysate from COS-7 cells which express CFTR (lane 1) and COS-7 cells which do not express CFTR (lane 2). Lanes 4, 6, 8, 10, and 12 are controls in which lysates from COS-7 cells which do not express CFTR were incubated with mAb 13-1 (lane 4), mAb 13-2 (lane 6), mAb 24-1 (lane 8), mAb 24-2 (lane 10), and pAb CFTR (lane 12).

Equivalents

Those skilled in the art will recognize, or be able to ascertain using no more than routine experimentation, many equivalents of the specific embodiments of the invention described herein. Such equivalents are intended to be encompassed by the following claims.

In support of this Patent, certain hybridoma cell lines have been deposited with the American Type Culture Collection, 12301 Parklawn Drive, Rockville Md. 20852, U.S.A. Pursuant to 37 CFR 1.808, all restrictions imposed by the depositor on the availability to the public of the below-listed deposits are irrevocably removed as of the issue date of this Patent.

(1) ATCC designation, HB 11946, hybridoma mAB 24-2, deposited Jun. 16, 1995.

(2) ATCC designation, HB 11947, hybridoma mAB 24-1, deposited Jun. 16, 1995

(3) ATCC designation, HB 10565, hybridoma mAb 13-1, deposited Sep. 27, 1990.

We claim:

1. A monoclonal antibody, mAb 13-1, produced from hybridoma cell line ATCC HB 10565.

2. A monoclonal antibody, mAb 24-1, produced from hybridoma cell line ATCC HB 11947.

3. A monoclonal antibody, mAb 24-2, produced from hybridoma cell line ATCC HB 11946.

4. A continuous hybridoma cell line having deposit accession number ATCC HB 10565, and clones thereof, which cell line produces monoclonal antibody to human CFTR.

5. A continuous hybridoma cell line having deposit accession number ATCC HB 11947, and clones thereof, which cell line produces monoclonal antibody to human CFTR.

6. A continuous hybridoma cell line having deposit accession number ATCC HB 11946, and clones thereof, which cell line produces monoclonal antibody to human CFTR.

7. A monoclonal antibody which binds an epitope comprising amino acids 729–736 of human CFTR.

8. A monoclonal antibody which binds an epitope comprising amino acids 1477–1480 of human CFTR.

9. A monoclonal antibody wich binds an epitope comprising amino acids 1433–1439 of human CFTR.

10. A kit for detecting human CFTR in a biological sample, said kit comprising:

(1) a container holding at least one monoclonal antibody selected from the group consisting of mAb 13-1, mAb 24-1, and mAb 24-2; and (2) instructions for using the antibody for the purpose of binding to human CFTR to form an immunological complex and detecting the formation of the immunological complex such that presence or absence of immunological complex correlates with presence or absence of human CFTR in said sample.

* * * * *